United States Patent
Flohr et al.

(10) Patent No.: US 9,414,797 B2
(45) Date of Patent: Aug. 16, 2016

(54) COMBINATION OF CONTRAST MEDIUM AND MAMMOGRAPHY CT SYSTEM WITH A PRESPECIFIED ENERGY RANGE AND METHOD FOR GENERATING TOMOGRAPHIC MAMMOGRAPHY CT IMAGES BY THIS COMBINATION

(71) Applicants: SIEMENS AKTIENGESELLSCHAFT, Munich (DE); BAYER PHARMA AKTIENGESELLSCHAFT, Berlin (DE)

(72) Inventors: Thomas Flohr, Uehlfeld (DE); Gregor Jost, Berlin (DE); Rüdiger Lawaczeck, Berlin (DE); Hubertus Pietsch, Kleinmachnow (DE); Bernhard Schmidt, Fuerth (DE)

(73) Assignees: Siemens Aktiengesellschaft, Munich (DE); Bayer Pharma Aktiengesellschaft, Berlin (DE)

( * ) Notice: Subject to any disclaimer, the term of this patent is extended or adjusted under 35 U.S.C. 154(b) by 247 days.

(21) Appl. No.: 14/028,815

(22) Filed: Sep. 17, 2013

(65) Prior Publication Data
US 2014/0086382 A1    Mar. 27, 2014

(30) Foreign Application Priority Data
Sep. 25, 2012 (DE) .......................... 10 2012 217 301

(51) Int. Cl.
*A61B 6/03*    (2006.01)
*A61B 6/00*    (2006.01)

(52) U.S. Cl.
CPC ................. *A61B 6/502* (2013.01); *A61B 6/032* (2013.01); *A61B 6/4007* (2013.01);
(Continued)

(58) Field of Classification Search
CPC .... A61B 6/032; A61B 6/4035; A61B 6/4042; A61B 6/481; A61B 6/482; A61B 6/502
USPC ............................... 378/9, 37, 98.9, 98.11, 16
See application file for complete search history.

(56) References Cited

U.S. PATENT DOCUMENTS

| 3,854,049 A | 12/1974 | Mistretta et al. |
| 3,974,386 A | 8/1976 | Mistretta et al. |

(Continued)

FOREIGN PATENT DOCUMENTS

| CN | 101044986 A | 10/2007 |
| CN | 102076263 A | 5/2011 |

(Continued)

OTHER PUBLICATIONS

W. Kalender et al., "High-resolution spiral CT of the breast at very low dose: concept and feasibility considerations", European Society of Radiology (2012) 22: pp. 1-8; 2012; DE.

(Continued)

*Primary Examiner* — Allen C. Ho
(74) *Attorney, Agent, or Firm* — Harness, Dickey & Pierce, P.L.C.

(57) ABSTRACT

A mammography CT system is disclosed which includes an X-ray generator; and a first radiator-detector system. A contrast medium, including an opacifying element including an absorption peak in a first energy range, is useable for tomographic imaging of a female breast of a patient. After filtering, the X-rays with a prespecified tube voltage that form at an anode, are configured to emit an X-ray spectrum having a second energy range, wherein the radiator-detector system is configured to acquire a plurality of circumferential projections around the breast. The first energy range is a part of the second energy range and the second energy range includes an upper limit of less than 70 keV and a lower limit of greater than 20 keV. A corresponding method for generating tomographic mammography CT images is also disclosed.

72 Claims, 4 Drawing Sheets

(52) U.S. Cl.
CPC ............ *A61B 6/4014* (2013.01); *A61B 6/4035* (2013.01); *A61B 6/4042* (2013.01); *A61B 6/481* (2013.01); *A61B 6/482* (2013.01)

(56) References Cited

U.S. PATENT DOCUMENTS

| | | | | |
|---|---|---|---|---|
| 6,195,580 | B1* | 2/2001 | Grable | 600/473 |
| 6,226,352 | B1* | 5/2001 | Salb | A61B 6/4035 378/143 |
| 6,614,878 | B2* | 9/2003 | Bogatu | A61B 6/4042 378/156 |
| 6,819,738 | B2* | 11/2004 | Hoffman | 378/19 |
| 6,891,918 | B2* | 5/2005 | Drummond et al. | 378/5 |
| 6,922,462 | B2* | 7/2005 | Acharya et al. | 378/98.11 |
| 6,950,492 | B2* | 9/2005 | Besson | A61B 6/508 378/16 |
| 6,999,549 | B2* | 2/2006 | Sabol | A61B 5/4872 378/5 |
| 7,010,092 | B2* | 3/2006 | Winsor | G01T 1/362 250/367 |
| 7,158,611 | B2* | 1/2007 | Heismann | A61B 6/4035 378/53 |
| 7,272,429 | B2* | 9/2007 | Walker | A61B 6/032 378/4 |
| 7,319,739 | B2* | 1/2008 | Heismann | A61B 6/032 378/5 |
| 7,327,826 | B2* | 2/2008 | Hanke et al. | 378/37 |
| 7,330,532 | B2* | 2/2008 | Winsor | G01T 1/362 250/367 |
| 7,457,450 | B2* | 11/2008 | Bruder | A61B 6/032 378/4 |
| 7,477,929 | B2* | 1/2009 | Klotz et al. | 600/431 |
| 7,583,779 | B2* | 9/2009 | Tkaczyk | A61B 6/032 378/5 |
| 7,649,981 | B2* | 1/2010 | Seppi et al. | 378/158 |
| 7,672,431 | B2 | 3/2010 | Lawaczeck et al. | |
| 7,697,657 | B2* | 4/2010 | Walter | A61B 6/4241 378/4 |
| 7,734,076 | B2* | 6/2010 | Du | A61B 6/032 378/16 |
| 7,856,134 | B2* | 12/2010 | Ruhmschopf | A61B 6/4241 382/128 |
| 7,869,563 | B2* | 1/2011 | Defreitas | A61B 6/502 378/114 |
| 7,869,862 | B2* | 1/2011 | Seppi | A61B 6/032 600/420 |
| 7,920,735 | B2* | 4/2011 | Krauss | A61B 6/482 378/21 |
| 8,064,986 | B2* | 11/2011 | Profio et al. | 600/425 |
| 8,197,437 | B2* | 6/2012 | Kalafut et al. | 604/67 |
| 8,422,636 | B2* | 4/2013 | Greenberg | G01T 1/29 378/207 |
| 8,442,184 | B2* | 5/2013 | Forthmann | A61B 6/032 378/5 |
| 2002/0031475 | A1 | 3/2002 | Speck et al. | |
| 2003/0103598 | A1 | 6/2003 | Bogatu et al. | |
| 2005/0031081 | A1 | 2/2005 | Winsor | |
| 2005/0084060 | A1 | 4/2005 | Green | |
| 2005/0123093 | A1 | 6/2005 | Lawaczeck et al. | |
| 2008/0013672 | A1 | 1/2008 | Krauss et al. | |
| 2011/0096892 | A1 | 4/2011 | Forthmann et al. | |
| 2011/0149068 | A1 | 6/2011 | Jeon | |
| 2012/0183726 | A1 | 7/2012 | Calkins | |

FOREIGN PATENT DOCUMENTS

| | | |
|---|---|---|
| CN | 103313658 A | 9/2013 |
| DE | 102006015451 A1 | 10/2007 |
| EP | 0994729 B1 | 4/2000 |
| EP | 0994729 B1 | 12/2002 |
| EP | 2168484 B1 | 10/2011 |
| WO | WO 98/58679 | 12/1998 |

OTHER PUBLICATIONS

Yaffe M.J.: "Digital Mammography", in: Handbook of Medical Imaging, 2000, vol. 1, pp. 329-372; 2000.

Lawaczeck R. et al.: "Dedicated Mammography: Imaging with monochromatic X-rays and clinical mammography unit", in: Nuclear Instruments and Methods in Physics Research, 2005, vol. 548, pp. 147-154; 2005.

Lawaczeck R. et al.: "New contrast media designed for x-ray energy subtraction imaging in digital mammography", in: Invest. Radiology, 2003, vol. 38, pp. 602-608; 2003.

Schmitzberger FF et al.: "Development of low-dose photon-counting contrast-enhanced tomosynthesis with spectral imaging", in: Radiology, 2011, vol. 259, pp. 558-564; 2011.

Fröling et al.: "Evaluation of Contrast Agent Kinetics for Contrast-enhanced Spectral Imaging of Breast Lesions in Comparison to MRI". In: RSNA Meeting 2011; 2011.

Callisen HH, et. Al.: "Absorbed dose in the presence of contrast agents during pediatric cardiac catheterization", in: Medical Physics, 1979, vol. 6, No. 6, pp. 504-509.

Chinese Office Action for CN Patent Application No. 2013104350739 dated Apr. 20, 2015.

\* cited by examiner

COMBINATION OF CONTRAST MEDIUM AND MAMMOGRAPHY CT SYSTEM WITH A PRESPECIFIED ENERGY RANGE AND METHOD FOR GENERATING TOMOGRAPHIC MAMMOGRAPHY CT IMAGES BY THIS COMBINATION

PRIORITY STATEMENT

The present application hereby claims priority under 35 U.S.C. §119 to German patent application number DE 102012217301.3 filed Sep. 25, 2012, the entire contents of which are hereby incorporated herein by reference.

FIELD

At least one embodiment of the invention generally relates to a system or combination of a contrast medium, which contains an opacifying element having an absorption peak in a first energy range, with a mammography CT system for the tomographic imaging of a female breast of a patient with a first radiator-detector system.

At least one embodiment of the invention also generally relates to a method for generating tomographic mammography CT images by a combination of a mammography CT system with an X-ray energy range which is to be set for scanning and a contrast medium which is to be selected, wherein the contrast medium primarily absorbs X-rays in a first energy range containing an absorption peak of an opacifying element and at least one second energy range used for the CT scan of the female breast is determined by setting an accelerating voltage and filtering the X-rays generated thereby.

BACKGROUND

In conventional mammography, a projection image is created of the compressed breast in the craniocaudal or lateral direction. The image shows a "shadow image" of the breast. Generally, tungsten (W)—or molybdenum (Mo)—and rhodium (Rh)—anodes with high voltages in the range up to 35 kV, rarely up to 49 kV, are used. The low-energy component of the X-rays emitted, which mainly contributes to the X-ray dose applied, but only little to the imaging, can also be separated with Mo-, Rh- or Cu filters depending upon the application.

Beam guidance and scattered light filters ensure high spatial resolution. Old-fashioned X-ray film has mostly been replaced by digital detectors. U. Speck & I. von Brenndorff describe contrast media for use in projection mammography in the publication EP 0 994 729 B1. However, when conventional contrast media containing iodine (I) with the atomic number $Z=53$ as an opacifying element are used, the potential of the contrast medium can only be used to an unsatisfactory extent since the emitted X-ray spectrum only overlaps unsatisfactorily with the K-edge of the iodine at 33 keV. If higher order elements are used, for example gadolinium (Gd) with the atomic number $Z=64$ and a K-edge of 50 keV, the disadvantages of this low degree of overlapping of X-ray energy and Gd absorption peak are even more noticeable. For these reasons alone, the application of contrast media has not become established in the field of conventional projection mammography.

The above-described conventional projection mammography has experienced a series of improvements at all levels in the last decade. On the excitation side, monochromatic X-rays have been tested, wherein a reduction in the X-ray dose compared to the use of polychromatic radiation is possible with the same contrast-to-noise ratio (CNR). When X-ray tubes with two anodes are used, it is possible to use contrast media where the K-edge of the absorbing element lies exactly between the two emission lines of the two anodes so that switching between the anodes, "turns" the visibility of the contrast medium "on or off". In principle, this enables the generation of subtraction images, which are virtually free of movement artifacts.

There have also been developments on the detector side—for example, nowadays energy-resolving detectors are available for a series of approaches. There has also been a gradual transfer to tomosynthetic representation by swiveling the tube and detector over the physiologically adapted clamped breast. At present, this development is tending toward CT devices that have been specially developed for breast imaging. As with conventional CT and MR imaging, in one possible embodiment, the woman lies on her stomach, only instead of the whole body, solely the breast is scanned without mechanical clamping. This produces 3D images such as those familiar from CT and MRI. However, specialization with regard to the breast enables a more economic and hence widely used device to be developed with high spatial and temporal resolution and used and marketed with a minimized X-ray dose. In this way, a device of this kind eliminates substantial drawbacks associated with conventional or traditional projection mammography, namely:

swinging from one breast to the other;
swinging from craniocaudal side to lateral;
mechanical compression of the breast;
movement artifacts, if the compression is changed or loosened in a sequence of two images;
no 3D images and
deficient temporal resolution for the use of contrast media in dynamic succession.

In traditional projection mammography, the application of contrast media was a major exception since, due to the compression of the breast, intact inflow into tumors was not guaranteed. Relief of the compression after unenhanced imaging for the application of contrast media with subsequent recompression automatically resulted in enormous movement artifacts. It is precisely this problem that is avoided with the use of the described CT mammography systems since the mammographic images are now obtained with the woman in prone position with a non-compressed breast, which also enables contrast medium to be applied to the prone patient without problems. In addition, the embodiment of X-ray source, the beam guidance and X-ray detection with energy resolution result in previously unknown possibilities for contrast-medium adaptation and beam reduction.

However, there is still the significant problem that, with the previous imaging with contrast media, the X-ray energy regions of the X-rays used and the main absorption regions of the contrast media used were unsatisfactorily matched to each other.

SUMMARY

At least one embodiment of the invention is directed to an improved combination of contrast medium and mammography CT system with which the X-ray energy used and the main absorption range of the contrast medium are better matched to each other. At least one embodiment is also directed to a correspondingly improved method for generating tomographic mammography images by use of such a combination of contrast medium and mammography CT system.

Advantageous developments of the invention are the subject matter of the subordinate claims.

The inventors have recognized that a combination that is optimized with regard to selection and adjustment of contrast medium with a mammography CT system enables scanning of a female breast with the minimum possible dose, wherein, on the one hand, it may be assumed that there are largely standard conditions present with respect to expected layer thicknesses and, on the other, it is also possible for a special adaptation of the limits of the set energy range of the X-rays to be performed, optionally by automated mechanisms, or integrated as an inherent property of the system. To this end, it is possible, for example for optical scanning and contour determination of the breast to be performed before the actual CT scanning. Here, it is particularly favorable if the breast to be examined is arranged in an uncompressed state in the measuring volume of the mammography CT system as a result of the corresponding positioning of the patient.

At least one embodiment of the invention is directed to a mammography CT system, comprising:

an X-ray generator; and a first radiator-detector system, wherein a contrast medium, including an opacifying element including an absorption peak in a first energy range, is useable for tomographic imaging of a female breast of a patient, and wherein, after filtering, the X-rays with a prespecified tube voltage that form at an anode, are configured to emit an X-ray spectrum having a second energy range, wherein the radiator-detector system is configured to acquire a plurality of circumferential projections around the breast, and wherein the first energy range is a part of the second energy range and the second energy range includes an upper limit of less than 70 keV and a lower limit of greater than 20 keV.

The inventors also suggest that the mammography CT system further comprise an apparatus for positioning the patient which permits uncompressed positioning of the breast in the measuring field of the at least one radiator-detector system during the CT scan. Here, the patient will preferably adopt a prone position so that the breasts can be scanned in their natural shape without any stressful pressure and deformation, wherein then substantially simpler local assignment of image positions to the real breast is possible.

The combination or system according to an embodiment of the invention can also be embodied such that the mammography CT system has a computer with a memory for program code and program code is stored therein, which, during operation, executes a method according to any one of the method claims below. It is also possible for at least one device, in particular switches, potentiometers or menu points in a parameterization menu, for adjusting the second energy range to be provided.

In addition to the above-described combination according to an embodiment of the invention of contrast medium and mammography CT system adapted to each other in an optimized way, the inventors also suggest a method for generating tomographic mammography images by a combination of a mammography CT system with an X-ray energy range to be set for scanning and a contrast medium to be selected, wherein:

the contrast medium primarily absorbs X-rays in a first energy range in which there is an absorption peak of an opacifying element and at least one second energy range used for the CT scan of the female breast is determined by setting an accelerating voltage and filtering the X-rays generated thereby.

BRIEF DESCRIPTION OF THE DRAWINGS

In the following, embodiments of the invention are described in more detail with reference to the figures, wherein only the features needed to understand embodiments of the invention are shown. The following reference characters are used: 1: mammography CT system; 2: rotating apparatus; 3: X-ray tube; 4: detector; 5: prefilter; 6: breast; 7: patient; 8: contrast medium application apparatus; 9: positioning apparatus; 10: computer; 11: laser range finder; A: anode; D: detector; EPh: photon energy; F: filter; P: object; Prg1-Prgn: computer programs T: tumor; W: window; τ: dwell time of the contrast medium in the tissue/tumor.

The individual figures show.

DETAILED DESCRIPTION OF THE EXAMPLE EMBODIMENTS

Figure 1:
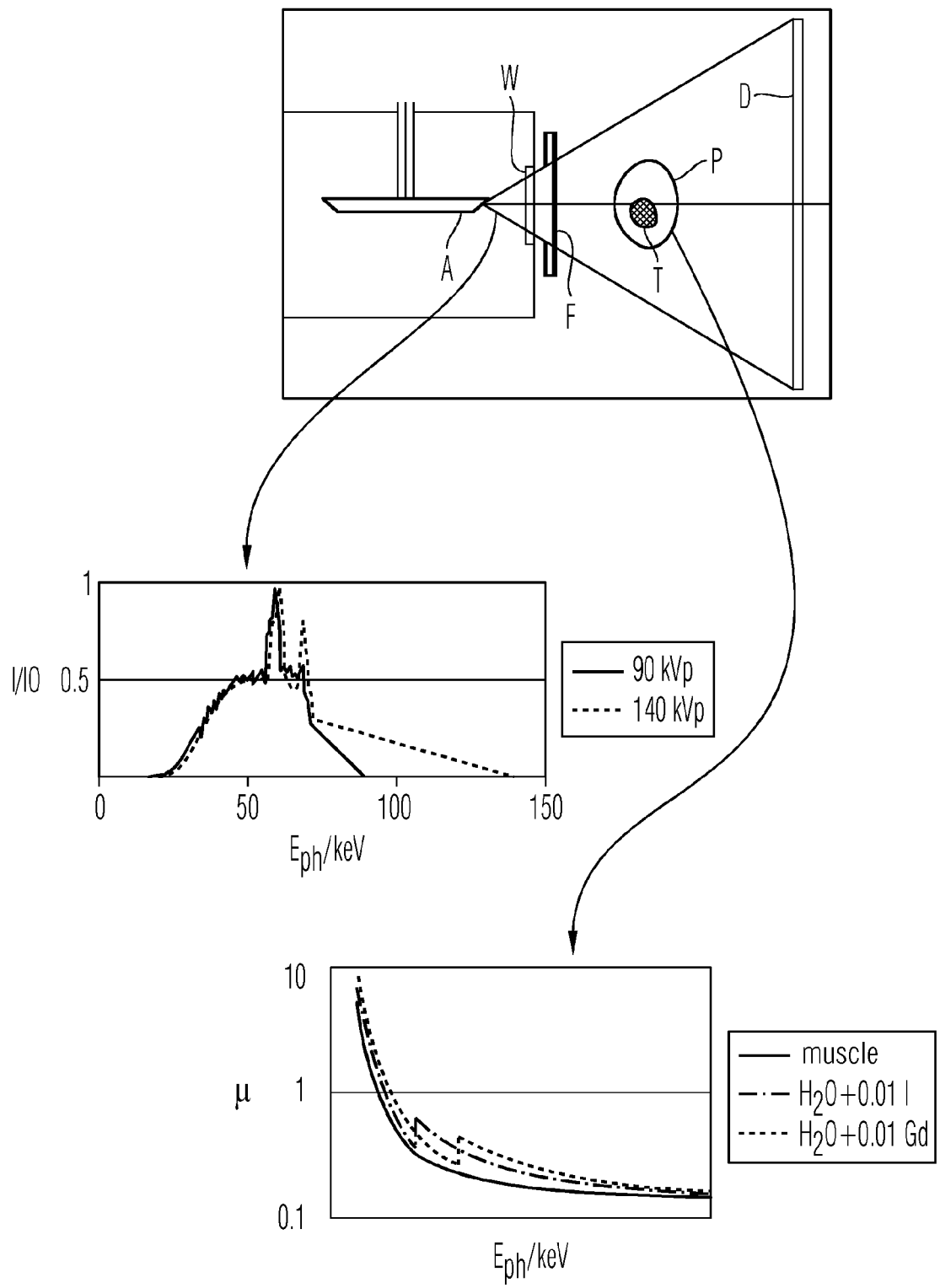
FIG. 1 a schematic representation for optimization of the combination of an X-ray spectrum to be set in conjunction with a contrast medium to be selected with respect to optimum contrasting with a simultaneously minimum dose application, FIG. 2 representation of the mass attenuation coefficients and of the mass energy attenuation coefficients in the region of the K-edge at 33 keV (left Y-axis) together with the DER against muscle tissue for iodine (right Y-axis), FIG. 3 optimized braking spectrum for an object with a 10 cm diameter using a tungsten anode in the energy range between 25 keV and 45 keV with the additional representation of second spectrum after prefiltering with iodine, FIG. 4 optimized braking spectrum for an object with 10 cm diameter using a tungsten anode in the energy range between 45 keV and 65 keV with additional representation of a second spectrum after prefiltering with gadolinium, FIG. 5 results of the concentration-time curves in the tumor after the administration of 0.1 mmol Gd kg−1 with a patient weighing 70 kg for four different dwell times with τ in seconds in the breast tumor, FIG. 6 examination results with a duration of application of 50 s with a total contrast medium dose of 37000 mg iodine and FIG. 7 mammography CT system.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors have recognized that a combination that is optimized with regard to selection and adjustment of contrast medium with a mammography CT system enables scanning of a female breast with the minimum possible dose, wherein, on the one hand, it may be assumed that there are largely standard conditions present with respect to expected layer thicknesses and, on the other, it is also possible for a special adaptation of the limits of the set energy range of the X-rays to be performed, optionally by automated mechanisms, or integrated as an inherent property of the system. To this end, it is possible, for example for optical scanning and contour determination of the breast to be performed before the actual CT scanning. Here, it is particularly favorable if the breast to be examined is arranged in an uncompressed state in the measuring volume of the mammography CT system as a result of the corresponding positioning of the patient.

It is particularly favorable with respect to the actually conflicting interests regarding optimal contrast-medium absorption properties to achieve the best contrast in tissue structures and the lowest possible energy deposition in the contrast-medium-enhanced tissue for the limits of the set X-ray energy range to be selected such that, by the choice of a lower limit that is not too low, the X-rays that cannot be used for the imaging are kept to a minimum, simultaneously for optimum contrasting by the selected contrast medium, the absorption peak of the contrast medium lies as completely as possible in the set X-ray energy range, but the set X-ray energy range extends as little as possible into the region of higher energy deposition. Here, it should be noted that, due to its intensified absorption, the contrast medium present in the tissue produces an increased dose compared to the case with tissue without contrast medium. The fact that not only the absorption of the photons, but also their flux and energy determines the deposited energy results in a further maximum of the deposited energy toward higher energies after a K-edge. Hence, it is desirable to place the upper limit of the set energy range above the K-edge, but beneath the subsequent maximum of a DER (dose enhancement ratio). Hence, DER should be understood to mean the ratio of the mass energy absorption coefficient $\mu_{en}$(tissue+contrast−medium)/$\rho$ of the tissue enhanced with contrast medium to the mass energy absorption coefficient $\mu_{en}$(tissue)/$\rho$. Therefore, the DER describes the factor of the dose increase produced by the addition of contrast medium. The following applies: DER=$a\cdot\mu_{en}$(tissue)/$\rho$+$b\cdot\mu_{en}$(contrast−medium)/$\rho$/$\mu_{en}$(tissue)/$\rho$, wherein a describes the relative tissue component and b the relative contrast medium component of the tissue-contrast medium mixture. An exemplary calculation with water as a tissue reference and iodine as the contrast medium produces a maximum of the DER with an X-ray energy of about 50 keV.

According to a further aspect of at least one embodiment of the invention, the inventors have also recognized that it is possible while using a mammography CT examination, in particular under the particular marginal conditions described here of the optimized combination of contrast medium and energy range of the mammography CT scanning, to differentiate tumors from healthy tissue if time constants for inflow and outflow of contrast medium in the tissue are determined. Here, in particular the dwell time $\tau$ of the contrast medium in the tissue can be used as a particularly characteristic time constant.

In accordance with these findings, the inventors suggest a combination of a contrast medium, which contains an opacifying element having an absorption peak (K-edge) in a first energy range, with a mammography CT system for the tomographic imaging of a female breast of a patient with a first radiator-detector system, which after filtering the X-rays with a prespecified tube voltage at an anode emits an X-ray spectrum having a second energy range, wherein the radiator-detector system acquires a plurality of circumferential projections around the breast, wherein, according to the invention, the first energy range is a part of the second energy range and the second energy range has an upper limit of less than 70 keV and a lower limit of greater than 20 keV.

In an example embodiment, the first energy range should begin with the increase in the absorption peak and extend until a drop in the absorption to no more than 60%, preferably to no more than 80%, of the maximum absorption value of the mass energy absorption coefficient in the absorption peak. Based on values of the mass absorption coefficients, the upper limit should be selected such that the absorption should not drop further than to 50%, preferably to no more than 60%, of the maximum mass absorption coefficient in the absorption peak.

Preferably, the mammography CT system is also embodied such that the first energy range is arranged in the upper half, preferably in the upper third, preferably in the upper quarter, of the second energy range.

In principle, the absorption peak described here can be any absorption edge (K- or L-edge) of an opacifying element, although in practice, due to the energy relation, primarily the K-edge of the opacifying element should be considered to be the absorption peak.

According to a special embodiment of the combination according to the invention, the second energy range can have an upper limit of between 40 keV and 45 keV, preferably with a lower limit of between 30 keV and 33 keV. Here, iodine is suggested as the opacifying element.

In another alternative, it is provided that the second energy range has an upper limit of between 50 keV and 60 keV, preferably in conjunction with a lower limit of between 40 keV and 50 keV, wherein here gadolinium is suggested as the opacifying element.

Metal filters can be used to set the lower limit of the second energy range, wherein particularly favorable is an arrangement of copper- and/or tin filters arranged in the region of the X-ray tubes in the beam path so that the radiation penetrating the object under examination is correspondingly prefiltered and there is no exposure to any radiation with X-ray energies which are anyway totally absorbed in the tissue.

Generally, according to an embodiment of the present invention, the second energy range should be set with respect to its upper limit such that, after the thickest tissue layer to be penetrated, taking into account the filtering, 60-90% of the photon flux is absorbed at maximum X-ray energy (=energy at the upper limit). In addition, the second energy range should be set with respect to its lower limit such that, after the thickest tissue layer to be penetrated, 90-60% of the photon flux is absorbed at the minimum X-ray energy (=energy at the lower limit).

To ensure that a sufficient dose arrives at the detector, care should be taken to ensure that the second energy range is selected such that, after the thickest tissue layer to be penetrated, the photon flux arriving at the detector is reduced to not less than 106 photons/(s*/mm$^2$). This consideration obviously also includes the dose rate that may be produced by the X-ray tube since this determines the initial photon flux.

As mentioned above, a further criterion for the selection of the optimum upper limit of the X-ray energy range emitted from the mammography CT system should also be the consideration of the contrast-medium-specific course of the DER. To this end, it is suggested that the second energy range has an upper limit which is selected such that it is arranged between the peak of the energy-specific absorption coefficient at the K-edge of the contrast medium and the next higher in terms of energy maximum of the DER (DER=dose enhancement ratio). This ensures that the lowest possible amount of X-ray energy is irradiated in a region into the tissue, which, due to the dose-increasing effect of the contrast medium, deposits a particularly high amount of energy in the tissue.

While, in principle, the combination according to an embodiment of the invention can be set on the basis of standard values with respect to the density and thickness of the breast tissue layers to be penetrated by radiation, it is, however, particularly advantageous for an apparatus for optically scanning the contour of the breast to be provided. This can, for example, be a LASER scanner, which is attached in the region of the radiator-detector system. Here, it is also possible to use the moving mechanism which rotates the radiator-detector system around the scanned region.

It is also possible for a device for the automatic determination of the thickest of the tissue layer to be penetrated by the X-rays to be provided. For example, due to the optically scanned contour or even a contour generated by a first rough overview scan with the CT, it is possible automatically to determine the maximal tissue layer to be penetrated and at the same time also its density, so that, on the basis of this data and the other criteria described, the applied X-ray energy range is set, and optionally also the automatic selection of the optimum contrast medium takes place, or at least optimum alternatives are made available in a selection menu.

In order to achieve a further improvement in the representation of a tomographically visualized breast, the combination according to at least one embodiment of the invention can also be equipped with a detector embodied as a direct-converting energy-resolving detector.

In addition, a second radiator-detector system arranged with an angular offset to the first, radiator-detector system can be provided to enable scanning from two projection directions to be performed simultaneously. This can achieve an improvement in the time resolution but, above all, it is also possible to perform simultaneous scanning with different energy ranges without using energy-resolving detectors.

The second radiator-detector system can preferably also have the above described features of the first radiator-detector system.

The inventors also suggest that the mammography CT system comprise an apparatus for positioning the patient which permits uncompressed positioning of the breast in the measuring field of the at least one radiator-detector system during the CT scan. Here, the patient will preferably adopt a prone position so that the breasts can be scanned in their natural shape without any stressful pressure and deformation, wherein then substantially simpler local assignment of image positions to the real breast is possible.

The combination according to an embodiment of the invention can also be embodied such that the mammography CT system has a computer with a memory for program code and program code is stored therein, which, during operation, executes a method according to any one of the method claims below. It is also possible for at least one device, in particular switches, potentiometers or menu points in a parameterization menu, for adjusting the second energy range to be provided.

In addition to the above-described combination according to an embodiment of the invention of contrast medium and mammography CT system adapted to each other in an optimized way, the inventors also suggest a method for generating tomographic mammography images by a combination of a mammography CT system with an X-ray energy range to be set for scanning and a contrast medium to be selected, wherein:

the contrast medium primarily absorbs X-rays in a first energy range in which there is an absorption peak of an opacifying element and at least one second energy range used for the CT scan of the female breast is determined by setting an accelerating voltage and filtering the X-rays generated thereby.

According to an embodiment of the invention, the first energy range and the at least one second energy range are selected such that the first energy range lies within the second energy range and the second energy range has an upper limit of less than or equal to 70 keV and a lower limit of greater than or equal to 20 keV.

Advantageously, the first energy range can be set such that it is arranged in the two upper thirds of the second energy range, preferably in the upper half of the second energy range or in the upper third of the second energy range.

In a favorable variant, the upper limit of the second energy range can be set to a value of between 40 keV and 45 keV and the lower limit to a value of between 30 keV and 33 keV, wherein preferably iodine can be used as the opacifying element. Here, in particular copper is suitable for filtering out the lower energy range. Due to the relatively low energy range, this setting variant is particularly suitable for examinations in which only relatively thin tissue layers have to be penetrated.

In another favorable variant, the upper limit of the second energy range can be set to a value of between 50 keV and 60 keV and the lower limit of the second energy range to a value of between 40 keV and 50 keV, wherein gadolinium can be used as the opacifying element. Here, preferably copper or even tin or a combination of the two can be used for the filtering. Due to the energetically higher energy range, a setting of this kind is particularly suitable for scanning relatively thicker tissue layers.

In principle, advantageously for the adaptation to tissue layer thicknesses penetrated by radiation, it is favorable for an upper limit for the second energy range to be selected such that, after the thickest tissue layer to be penetrated, taking into account the prefiltering, 60% to 90% of the photon flux is absorbed at the maximum X-ray energy, while the lower limit should be selected such that the thickest tissue layer to be penetrated absorbs 90% to 60% of the photon flux at the minimum X-ray energy.

To obtain good measuring results, the second energy range should also be selected such that, after the thickest tissue layer to be penetrated, the photon flux arriving at the detector falls to not less than 106 photons (s*/mm$^2$).

In order to avoid the measurement resulting in an excessive input of energy into the examined breast, it is also favorable for the upper limit of the second energy range to be selected such that it is arranged between the peak of the energy-specific absorption coefficient at the K-edge of the contrast medium and the next higher in terms of energy maximum of the DER. In this way, on the one hand, optimum use is made of the opacifying effect of the contrast medium while, on the other, an unnecessarily high dose load is avoided.

With this method, it is possible, optionally performed automatically by the mammography CT system, for optical scanning of the contour of the breast to be performed before the actual CT scanning. For example, the optical scanning can be performed with the aid of at least one LASER scanner, wherein said scanner should preferably be arranged in the region of the radiator-detector system, preferably on a rotating apparatus bearing the at least one radiator-detector system. In the simplest case, it is possible, for example, to use a plurality of LASER range finders arranged one on top of the other, which, together with the rotating gantry, move round the breast located in the examination field and, by determining the distance between surface of the breast and their rotation path in a plurality of planes, determine the contour. This makes it possible in a very simple way to determine the thickest tissue layer to be penetrated by radiation before the actual CT scanning.

Alternatively, it is also possible with the aid of a, preferably coarse, prescan with X-rays, to determine the contour of the breast and at the same time also the present tissue thickness so that the, preferably then subsequent setting of the energy ranges used—and hence optionally also the selection of a contrast medium—can be performed automatically taking into account the current conditions of absorption by the breast to be scanned.

It can also be advantageous during the performance of the CT scan for the attenuation of the X-rays to be determined specifically for the energy range. Various procedures are suitable for this. For example, a single radiator-detector system could perform two or more CT scans each with a differently set second energy range. This results in a plurality of absorption spectra.

In another variant, it is possible to use a dual source system with which two scans are performed simultaneously with two radiator-detector systems arranged with an angular offset each with different second energy ranges.

Alternatively, at least one scan can be performed with a radiator-detector system having at least one energy-range-resolving detector, wherein the measured attenuations are divided into at least two different energy ranges. In this case, preferably at least one direct-converting detector is used.

If two different spectra are used for the examination, the distribution of the spectra used should be matched to each other such that the entire photon flux per spectrum differs by no more than 50%, preferably no more than 30%, preferably no more than 20%, preferably no more than 10%.

If the above-described examinations provide energy-range-specific attenuation data, this energy-range-specific attenuation data can be used to break the material of the tomographic mammography images down into at least two materials. Preferably, the material breakdown can break the tomographic images down into at least two of the components soft tissue, calcium and contrast medium, which can then be used as a basis for differential diagnosis.

According to the second aspect of an embodiment of the present invention, the inventors also suggest that a mammographic CT examination of the uncompressed breast with inflow and outflow of contrast medium, preferably with the same image parameters, be used to generate a time series consisting of several, preferably at least three, chronologically successive tomographic mammography CT images.

This makes it possible to determine at least one first time constant in the time series describing the time response of the inflow or to determine at least one second time constant describing the time response of the outflow of contrast medium. It is possible, for example, to determine the dwell time of the contrast medium in the tissue as a characteristic time constant. Here, it is assumed that there is an exponential time response of the concentration K(t) in the tissue, which can be described approximately by the equation $K(t)=K_{max} \exp(-t/\tau)$. Here, $\tau$ corresponds to the decay time required to reach 1/e of the maximum concentration $K_{max}$. However, reference is made to the fact that the method according to the invention is not solely restricted to this partial exponential behavior and other approximation methods with other functions belong to the invention.

The typical differences between benign and malignant tissue result in different time constants for the inflow and outflow of contrast medium so that a volume-specific determination of such time constants can be used to support the diagnosis. It is therefore also suggested that the time constant is determined volume-specifically over the volume of the breast and the values of at least one volume-specifically determined time constant are output in a tomographic representation.

Preferably, a tomographic mammography CT representation can be displayed superimposed with the tomographic representation of the at least one time constant, wherein it is favorable if, with the superimposed representation of the at least one tomographic mammography CT representation with the tomographic representation of the at least one time constant, the CT values of the mammography CT representation are shown in black and white and the time constant is shown in color.

In addition to the combination of contrast medium and mammography CT system described here adapted to each other in an optimized way on the one hand and the method described here for generating tomographic mammography images by such a combination of a mammography CT system with an X-ray energy range which is set optimally for scanning and a selected contrast medium on the other, an embodiment of the invention also includes the production and provision of a combination of this kind and/or of a contrast medium with the indication for use with the method described here with a mammography CT system set in accordance with the above-described criteria.

To use contrast media in X-ray CT-mammography, it is necessary to combine physical, pathophysiological and pharmacokinetic conditions in an appropriate way, only then can the use of contrast medium extend beyond unenhanced morphological diagnosis.

Physical conditions include optimum combination of the X-ray spectrum with the absorption properties of the contrast medium induced by the opacifying element, for example iodine (I) or gadolinium (Gd). In the case of a conventional CT device, the choice of parameters is limited because, in the majority of cases only the high-voltage range from 80 to 140 kV is available. In addition to these pure absorption properties, which are ultimately described by a type of Lambert-Beer law, care must be taken to ensure that the level of the doses through the contrast medium remains within acceptable limits or is insignificant. Therefore, the X-ray spectrum needs to be adjusted by the choice of anode, high voltage and filtering such that X-ray absorption is optimized with an acceptable dose level. Finally, these optimization considerations should also include the size of the breast. Hitherto, the inclusion of the dose increase necessitated by the contrast medium has been completely disregarded.

FIG. 1 is a schematic representation for the optimization of a combination of an X-ray spectrum to be set in conjunction with a contrast medium to be set with respect to optimum contrast with a simultaneously minimum dose level. The top diagram is a schematic view of a mammography CT system in section with which X-rays are generated at an X-ray tube with an anode A, filtered after leaving through the window W by a filter F and measured at the detector D. The X-ray spectrum generated here is shown using the example of a tungsten anode with 90 kVp and 140 kVp accelerating voltage in the diagram shown on the left underneath. The standardized intensity I/I0 is plotted over the photon energy Eph.

Also schematically shown in the beam path, is an object P with contrast-medium-enhanced tissue in a subarea T (=tumor). The corresponding absorption behavior is shown in the lower diagram for muscle tissue, water with 1% iodine and water with 1% gadolinium with the corresponding curves of the mass absorption coefficients μ on a logarithmic scale over the photon energy EPh.

Apart from pure "still pictures", which intensify the morphological contrast from normal tissue, the pharmacokinetics also provide additional diagnostic information. If the knowledge of contrast-medium-supported MR mammography is transferred to targeted CT mammography, benign and malignant tumors can be expected to have different pharmacokinetics. Benign tumors frequently reveal a steady inflow for up to 700 s after application, malignant tumors respond with a rapid increase followed by a "wash-out". In addition, there are also fewer unambiguous cases. Based on new contrast medium-whole-body-pharmacokinetics, which place the emphasis on blood half-life times, it is also possible to model tumors by introducing tumor-blood-half-life times. Here, surprisingly, a parameter τ for the blood or plasma half-life time of the tumor is sufficient to differentiate between benign and malignant tumors. Due to the unavoidable dose loads, when used on humans, there are restrictions with respect to a continuous sequence of images. However, it is sufficient in each case to use only two to three contrast-medium images in addition to the non-enhanced image. Surprisingly, when choosing times, the kinetic model can define precise patient-specific times. For a mammography CT examination, it is necessary to apply about 100 ml of a more viscous contrast-medium. The application bolus can be varied within wide ranges with respect to rate of application and concentration of the contrast-medium solution.

Figure 2:
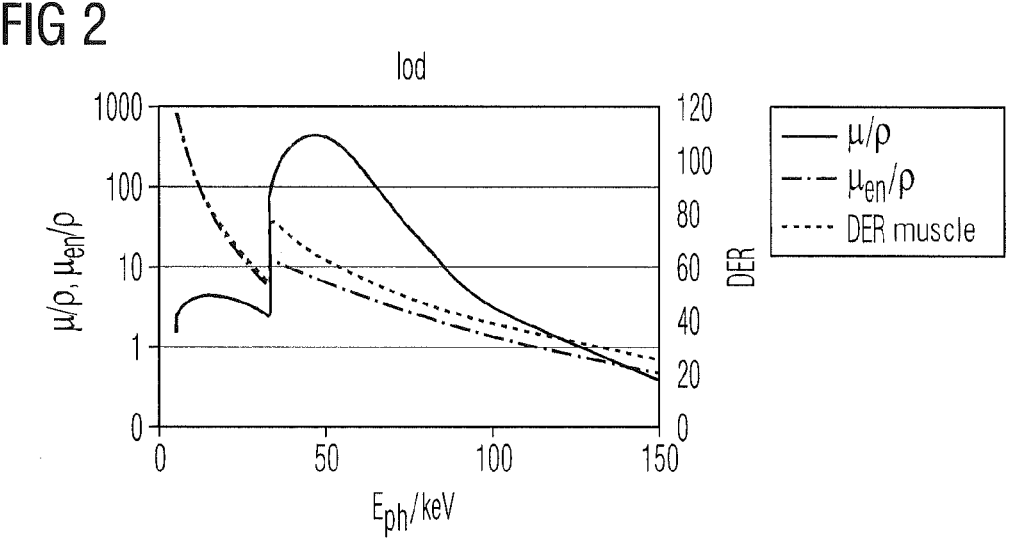

FIG. 2 shows the mass attenuation coefficients μ/ρ and the mass energy attenuation coefficient μen/ρ with the K-edge leap at 33 keV (left Y-axis) together with the "dose enhancement ratio" (DER, compared to muscle tissue) for iodine (right Y-axis). The DER represents the intensification of the X-ray dose administered through the contrast medium and behaves additively with respect to the X-ray dose administered externally. The photon energy EPh is plotted on the X-axis.

In order to optimize the absorption for the contrasting in the mammography CT image, the X-ray spectrum should be started at energies of E>33 keV and, to reduce the dose increase due to the iodine-contrast medium, the maximum of the DER course avoided, i.e. E<40-45 keV or 30-33 keV<E<40-45 keV for iodine.

Figure 3:
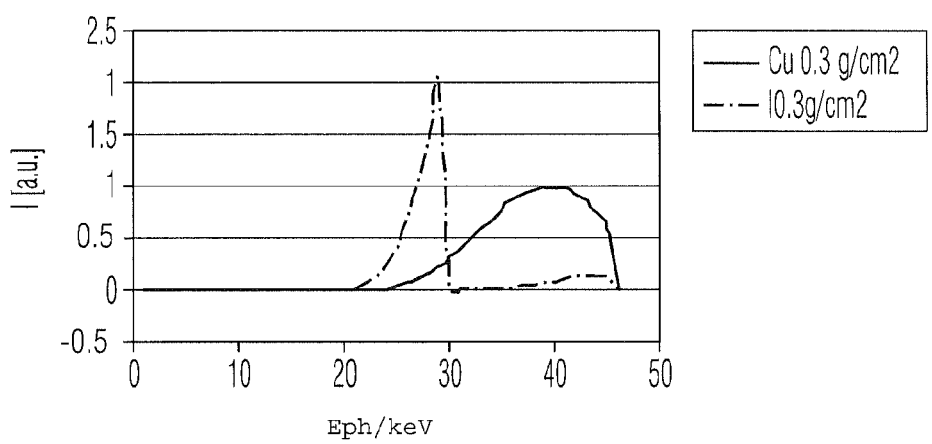

In FIG. 3, the solid line shows by way of example, with the assumption of an object with a diameter of 10 cm and the use of a tungsten anode, a spectrum which has been optimized appropriately for this with intensity values I on the Y-axis for the use of an iodine-contrast medium with a K-edge at 33 keV over the photon energy EPh. For the optimization of the spectrum, a filter with 0.3 g/cm³ copper was used for the prefiltering of radiation and the accelerating voltage adapted to the contrast medium iodine with 45 kVp.

Figure 4:
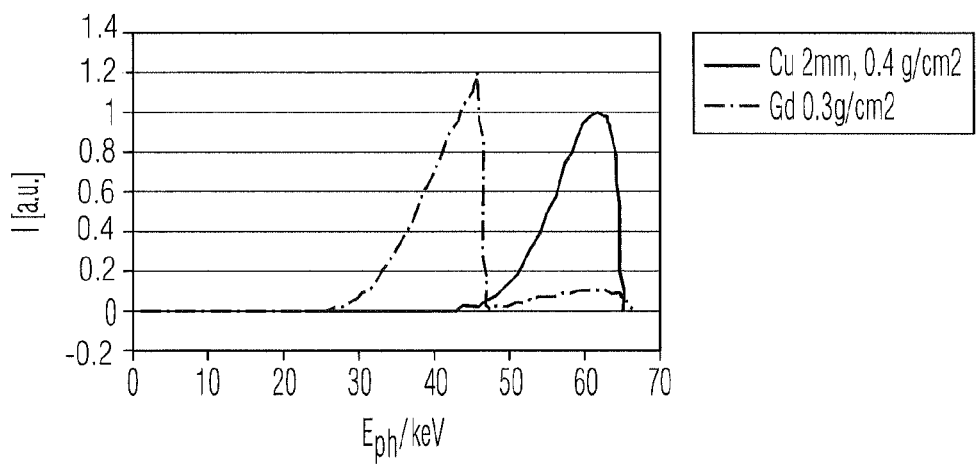

In FIG. 4, also with the assumption of an object with 10 cm diameter and the use of a tungsten anode, the solid line depicts a spectrum which has been optimized for this object in combination with the use of a gadolinium-contrast medium with a K-edge at 50 keV. For the optimization of the spectrum, a filter with 2.0 g/cm³ copper and 0.4 g/cm³ tin was used for the prefiltering of the radiation and the accelerating voltage was adapted to the contrast medium used with 65 kVp.

Since for the material used as the anode, tungsten, has its K-edge at 69.5 keV and its L-edges between 10 keV and 12 keV, there is no intensity peak in the braking spectrum shown.

However, in the case of a dual-energy technique with K-edge-imaging, both FIG. 3 and FIG. 4 also depict by way of a dot-dash line a second advantageous optimized spectrum with a center of gravity below the K-edge of the contrast medium used in each case. This spectral course is achieved in that the radiation is prefiltered with the same material that is used as the contrast medium. Therefore, for this, in FIG. 3 iodine is used as the prefilter material and in FIG. 4 gadolinium. Filtering of this kind can be achieved for example in that the contrast medium, here the iodine or gadolinium, is preferably finely distributed, enclosed in a plastic material and the mixture of plastic and contrast medium is introduced into the beam path.

When an energy-resolving detector is used, this additional prefiltering can be omitted since the separation of the energies above and below the K-edge is achieved by a corresponding choice of detector energy thresholds.

Figure 5:
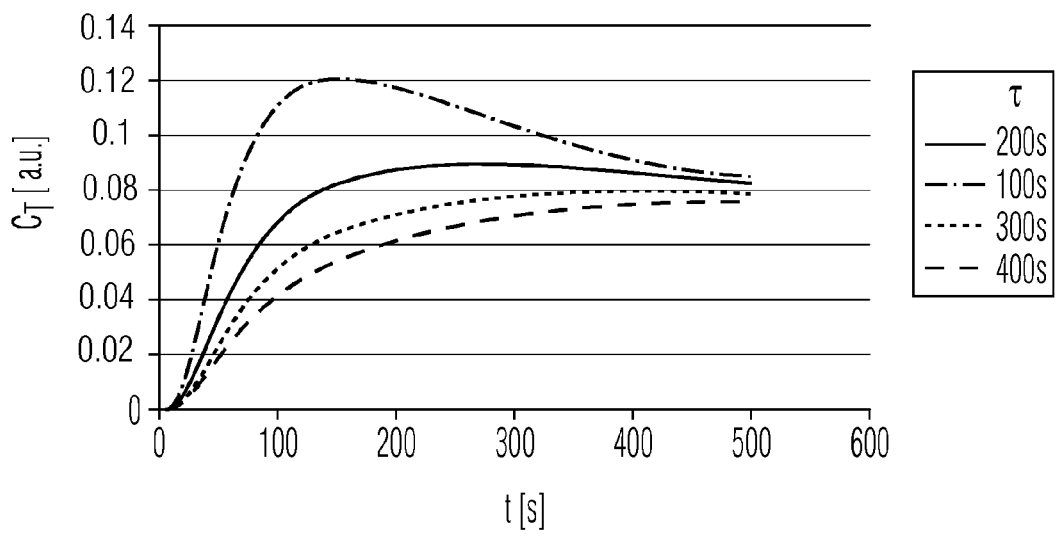

FIG. 5 summarizes the results of the concentration-time curves in the tumor after the administration of 0.1 mmol Gd kg−1 in the case of a patient weighing 70 kg for four different dwell times with τ in seconds in the breast tumor. The time t after application is plotted in seconds on the X-axis. Here, a differentiation is made between three types of curves. In the case of benign tumors, a continuous increase in the concentration CT in the tumor is observed, as is shown for the τ-values of 300 s and 400 s in the diagram. Malignant tumors are often characterized by a rapid increase with a subsequent reduction in concentration, as can be seen for τ=100 s. The curve with τ=200 s roughly speaking identifies the region between malignant and benign tumors. These are one-parameter representations, wherein τ describes the dwell time in the tumor due to the blood flow and the following applies: $\tau=V_T/k_T$, with the tumor volume VT and the tumor blood flow kT.

It has been found that the results determined with CT can be described well by a kinetic model, however, consideration should also be paid to the fact that in the case of X-ray examinations and the use of CT-values or Hounsfield units (HU), the latter are linearly dependent on the concentration of the contrast medium.

FIG. 5 also shows that, due to the higher flow rates, that is at low τ-values, with identical tumor volumes, the concentration of the contrast medium for malignant tumors in each case achieves higher values.

Figure 6:
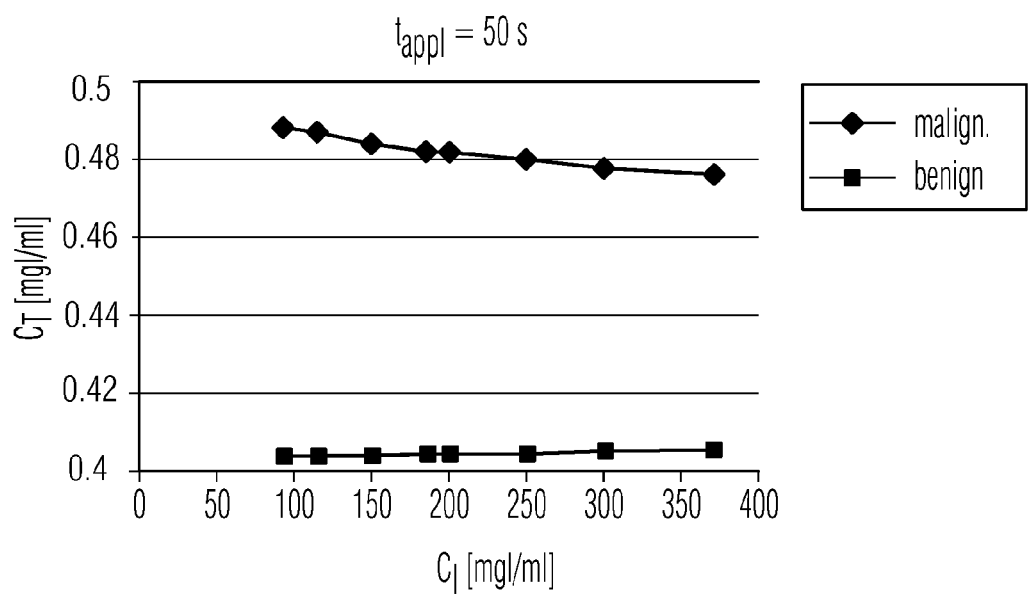

The same observation is made for bolus applications as shown in FIG. 6. This figure shows examination results with a duration of application tappl of 50 s with a total contrast-medium dose of 37000 mg iodine. The contrast-medium concentration CT in the tumor over time is shown on the Y-axis and the concentration CI of the iodine solution in mg I/ml is shown on the X-axis. The values for malignant tumors are plotted as rhombuses and those for benign tumors as squares. The dose can be applied with an application rate of 2 ml s−1 with an iodine solution concentration of 370 mg I ml−1 up to 8 ml s−1 for an iodine-concentration of 92.5 mg I ml−1. 115 mg I ml−1 are approximately isotonic with blood. It is evident that it is favorable with malignant tumors to work with small iodine concentrations but high application rates, in the case of benign tumors, the effect is negligible. It is obviously also possible to vary the duration of application, but, in order not to distress the patient unduly, the period of application should not be arbitrarily extended and should remain below 100 s.

In order to generate the lowest possible radiation level, the mammography CT examination described here is concentrated on a few temporal measuring points, wherein tomographic representation of the dwell times τ are generated from these measuring points pixel-by-pixel or voxel-by-voxel. A simultaneously optimized combination between the contrast medium and mammography CT system with the X-ray energy range set enables a particularly low X-ray dose level to be achieved.

Hence, the subject matter of this application meets modern requirements for dose-optimized X-ray CT imaging using device and contrast-medium parameters which are optimally matched to each other and preferably also personalized for the patient to be examined.

Therefore, the combination and the method described avoid the drawbacks of conventional mammography by way of:
- optimization of the energy spectrum of the X-rays used for the object set,
- minimization of the X-ray dose,
- avoidance of the compression of the breast by physiological positioning in the prone position,
- tomographic imaging in 3D,
- optimum overlapping of X-ray spectrum and contrast medium absorption,
- avoidance of the energy range of the maximum dose increase due to the contrast medium,
- high spatial resolution without movement artifacts, high temporal resolution,
- application of the contrast medium in the prone position,
- personalized adaptation of the application profile and
- the use of energy-resolving detectors or other dual energy techniques for separating and quantifying the tissue and contrast medium contrast.

Figure 7:
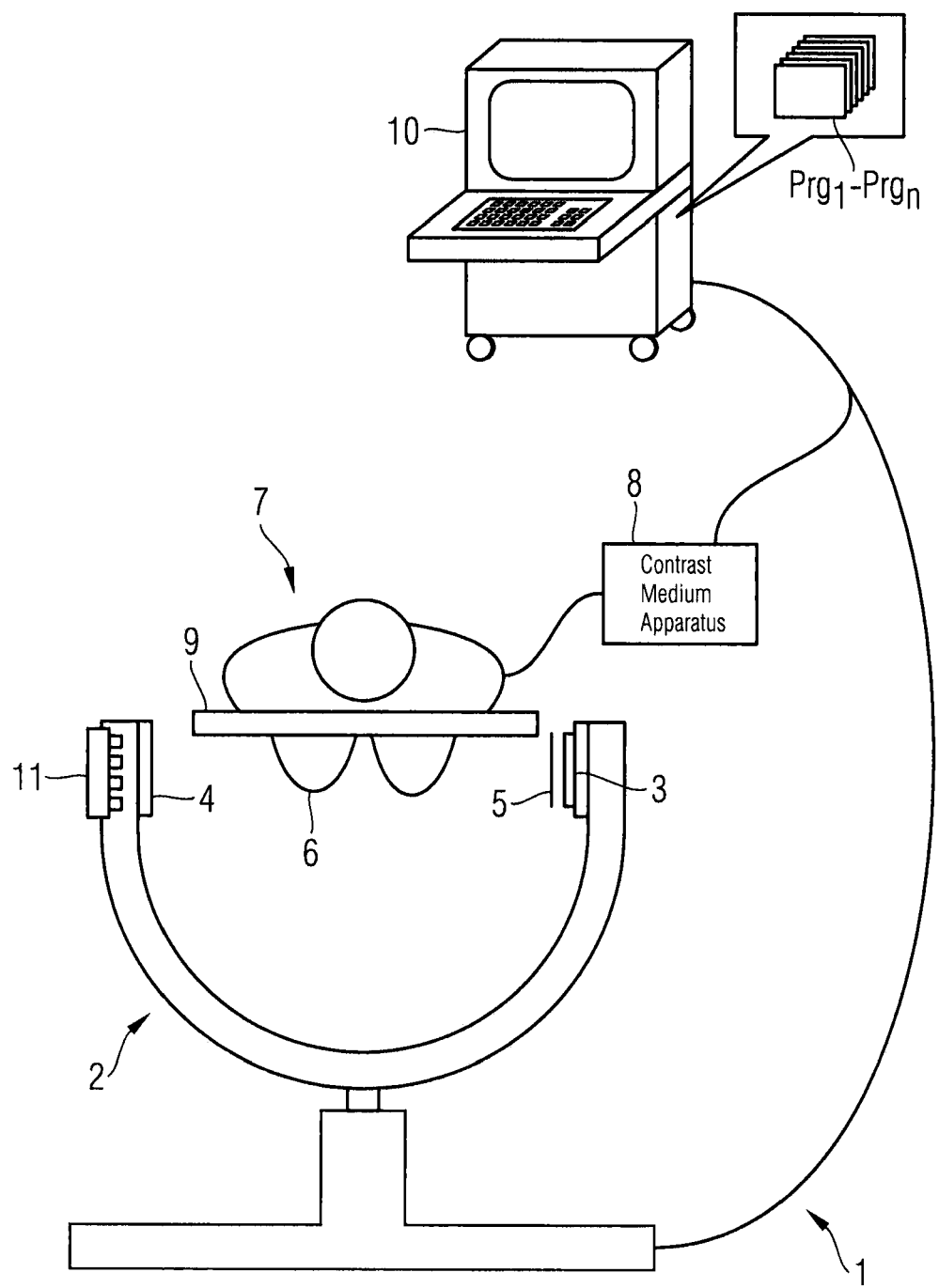

A schematic representation of a mammography CT system 1 equipped according to the invention is shown in FIG. 7. This shows a rotating apparatus 2, to which a radiator-detector system comprising an X-ray tube 3 with a prefilter 5 and a detector 4 arranged opposite thereto, is attached. In addition, a positioning apparatus 9 for a patient 7 is arranged so that the breast 6 of the patient 7 can be positioned without compression in the measuring field of the rotatable radiator-detector system. In addition, the mammography CT system 1 also comprises an automatic contrast medium application apparatus 8 for the automatically controlled application of a contrast medium which was chosen in advance in accordance with the above specifications. The mammography CT system 1 and the contrast medium application apparatus 8 are controlled by a computer 10, which contains in its memory programs Prg1-Prgn which are executed during operation.

For scanning the contour of the breast, a series of LASER range finders 11 arranged one on top of the other is attached to an arm of the rotating apparatus 2 with the aid of which the contour of the uncompressed breast which is already located in the measuring field of the radiator-detector system can be determined before the X-ray scanning. Alternatively, it is also possible to determine the contour and density distribution of the breast in advance solely by way of the radiator-detector system with the aid of a prescan.

According to an embodiment of the invention, the mammography CT system 1—here embodied by corresponding menu points, which can be selected via a keyboard or another usual type of input device—comprises an input device controlled by programming technology, which, preferably in dependence on the pre-determined contour of the breast and layer thicknesses to be penetrated by radiation determined therefrom—suggests at least one optimized combination of a set X-ray energy range with a contrast medium to be automatically applied. The choice of one of the suggested combinations then enables the actual mammography CT scanning to be performed under optimized conditions.

If the system 1 suggested here generates a time sequence of CT images with the inflow and outflow of contrast medium, by using appropriately written computer programs, with this system, the method according to the invention can also be used for the determination of the volume-specific dwell time τ of contrast medium in the tissue.

Although the invention was illustrated and described in more detail by the preferred example embodiment, the invention is not restricted by the disclosed examples and other variations can be derived herefrom by the person skilled in the art without departing from the scope of protection of the invention.

What is claimed is:

1. A mammography CT system configured to perform a CT scan, comprising:
   a contrast medium application apparatus configured to supply a contrast medium to a patient, the contrast medium including an opacifying element having an absorption peak in a first energy range, the first energy range falling within a second energy range and the absorption peak being a K-edge of the opacifying element;
   an x-ray generator including a cathode and an anode, the x-ray generator configured to emit x-rays towards a breast of the patient lying in a prone position, the anode having an acceleration voltage applied thereto;
   a prefilter configured to prefilter the x-rays before the x-rays reach the breast; and
   a computer configured to,
      determine a lower limit of the second energy range such that the lower limit is set based on a minimum energy absorbable by the breast and is greater than or equal to 20 keV,
      determine an upper limit of the second energy range for the CT scan of the breast such that the upper limit is above the k-edge of the opacifying element, below a subsequent maximum dose enhancement ratio (DER) of the contrast medium and less than or equal to 70 keV,
      set the accelerating voltage of the x-ray generator such that a maximum energy of the x-rays that are emitted is the upper limit of the second energy range, the absorption peak of the opacifying element being below the upper limit of the second energy range, and
      configure the pre-filter such that the pre-filter filters the x-rays to have a minimum energy equal to the lower limit of the second energy range, the absorption peak of the opacifying element being above the lower limit of the second energy range.

2. The mammography CT system of claim 1, wherein the first energy range begins with the increase in the absorption peak and extends until a drop in the absorption to not more than 60% of the maximum absorption value of the mass energy absorption coefficient in the absorption peak.

3. The mammography CT system of claim 2, wherein the first energy range is arranged in the upper third of the second energy range.

4. The mammography CT system of claim 2, wherein the first energy range is arranged in the upper quarter of the second energy range.

5. The mammography CT system of claim 1, wherein the first energy range is arranged in the upper third of the second energy range.

6. The mammography CT system of claim 5, wherein the first energy range is arranged in the upper quarter of the second energy range.

7. The mammography CT system of claim 1, wherein the first energy range is arranged in the upper quarter of the second energy range.

8. The mammography CT system of claim 1, wherein the second energy range has an upper limit of between 40 keV and 45 keV.

9. The mammography CT system of claim 1, wherein the second energy range has a lower limit of between 30 keV and 33 keV.

10. The mammography CT system of claim 1, wherein the opacifying element is iodine.

11. The mammography CT system of claim 1, wherein the second energy range has an upper limit of between 50 keV and 60 keV.

12. The mammography CT system of claim 1, wherein the second energy range has a lower limit of between 40 keV and 50 keV.

13. The mammography CT system of claim 1, wherein the opacifying element is gadolinium.

14. The mammography CT system of claim 1, wherein the prefilter includes copper or tin, and the prefilter is arranged in beam path of the x-rays.

15. The mammography CT system of claim 1, wherein the second energy range has an upper limit which is selected such that, after the thickest tissue layer to be penetrated by x-rays, taking into account the prefilter, between 60% to 90% of the photon flux is absorbed at the maximum X-ray energy.

16. The mammography CT system of claim 15, wherein the second energy range has a lower limit which is selected such that, after the thickest tissue layer to be penetrated, 90% to 60% of the photon flux is absorbed at the minimum X-ray energy.

17. The mammography CT system of claim 1, wherein the second energy range has a lower limit which is selected such that, after the thickest tissue layer to be penetrated by x-rays, 90% to 60% of the photon flux is absorbed at the minimum X-ray energy.

18. The mammography CT system of claim 1, wherein the second energy range is selected such that, after the thickest tissue layer to be penetrated by x-rays, the photon flux arriving at a detector is reduced to not less than $10^6$ photons/(s*/mm$^2$).

19. The mammography CT system of claim 1, wherein the second energy range has an upper limit which is selected such that it is arranged between the peak of the energy-specific absorption coefficient at the K-edge of the opacifying element and the next higher in terms of energy maximum of the DER between tissue and contrast-medium enhanced tissue.

20. The mammography CT system of claim 1, further comprising:
   an apparatus for optically scanning a contour of the breast.

21. The mammography CT system of claim 20, wherein the apparatus is a LASER scanner.

22. The mammography CT system of claim 21, wherein the computer is configured to automatically determine the thickest tissue layer to be penetrated by the X-rays based on data from the LASER scanner.

23. The mammography CT system of claim 1, further comprising:
   a detector configured as a direct-converting energy-resolving detector.

24. The mammography CT system of claim 1,
   wherein the x-ray generator forms a first radiator-detector system, and the system further comprises:
   a second radiator-detector system, arranged with an angular offset to the first radiator-detector system.

25. The mammography CT system of claim 24, wherein the second radiator-detector system has a first energy range that begins with the increase in the absorption peak and extends until a drop in the absorption to not more than 60% of the maximum absorption value of the mass energy absorption coefficient in the absorption peak.

26. The mammography CT system of claim 24, wherein the prefilter includes the opacifying element of the contrast medium, arranged in the beam path of the first radiator-detector system.

27. The mammography CT system of claim 24, wherein the prefilter includes the opacifying element of the contrast medium, and the prefilter is arranged in a beam path of at least the first radiator-detector system.

28. The mammography CT system of claim 1, further comprising:
an apparatus configured to position the patient, which permits uncompressed positioning of the breast during the CT scan.

29. The mammography CT system of claim 1, wherein the computer includes a memory storing program code and program code segments therein which, during operation, executes:
determining the first energy range, wherein the contrast medium primarily absorbs X-rays in the first energy range, the first energy range including an absorption peak of the opacifying element such that the at least one first energy range lies within the at least one second energy range.

30. The mammography CT system of claim 1, further comprising:
switches, potentiometers or menu points in a parameterization menu, for adjusting the second energy range.

31. A method for determining X-ray energy ranges, the method comprising:
supplying a contrast medium to a patient, the contrast medium including an opacifying element having an absorption peak in a first energy range, the first energy range falling within a second energy range and the absorption peak being a K-edge of the opacifying element;
emitting, via an x-ray generator including a cathode and an anode, x-rays towards a breast of the patient lying in a prone position, the anode having an acceleration voltage applied thereto;
prefiltering, via a prefilter, the x-rays before the x-rays reach the breast;
determining, via a computer, a lower limit of the second energy range such that the lower limit is set based on a minimum energy absorbable by the breast and is greater than or equal to 20 keV;
determining, via the computer, an upper limit of the second energy range for the CT scan of the breast such that the upper limit is above the k-edge of the opacifying element, below a subsequent maximum dose enhancement ratio (DER) of the contrast medium and less than or equal to 70 keV;
setting, via the computer, the accelerating voltage of the x-ray generator such that a maximum energy of the x-rays that are emitted is the upper limit of the second energy range, the absorption peak of the opacifying element being below the upper limit of the second energy range; and
configuring, via the computer, the pre-filter such that the pre-filter filters the x-rays to have a minimum energy equal to the lower limit of the second energy range, the absorption peak of the opacifying element being above the lower limit of the second energy range.

32. The method of claim 31, further comprising:
setting the first energy range such that it is arranged in the two upper thirds of the second energy range.

33. The method of claim 32, wherein the setting the first energy range includes setting the first energy range such that it is arranged in the upper half of the second energy range.

34. The method of claim 32, wherein the setting the first energy range includes setting the first energy range such that it is arranged in the upper third of the second energy range.

35. The method of claim 31, further comprising:
setting the first energy range such that it is arranged in the upper half of the second energy range.

36. The method of claim 35, wherein the setting the first energy range includes setting the first energy range such that it is arranged in the upper third of the second energy range.

37. The method of claim 31, further comprising:
setting the first energy range such that it is arranged in the upper third of the second energy range.

38. The method of claim 31, further comprising:
setting an upper limit of the second energy range to a value of between 40 keV and 45 keV.

39. The method of claim 31, further comprising:
setting the lower limit of the second energy range to a value of between 30 keV and 33 keV.

40. The method of claim 31, wherein the opacifying element is iodine.

41. The method of claim 31, further comprising:
setting an upper limit of the second energy range to a value of between 50 keV and 60 keV.

42. The method of claim 31, further comprising:
setting the lower limit of the second energy range to a value of between 40 keV and 50 keV.

43. The method of claim 31, wherein the opacifying element is gadolinium.

44. The method of claim 31, wherein the prefiltering includes using copper or tin for filtering the X-rays.

45. The method of claim 31, further comprising:
selecting an upper limit for the second energy range such that after the thickest tissue layer to be penetrated by x-rays and, taking into account prefiltering, 60% to 90% of the maximum X-ray energy is absorbed.

46. The method of claim 31, further comprising: selecting a lower limit of the second energy range such that, after the thickest tissue layer to be penetrated by x-rays and taking into account prefiltering, 90% to 60% of the photon flux is absorbed at the minimum X-ray energy.

47. The method of claim 31, further comprising:
selecting the second energy range such that, after the thickest tissue layer to be penetrated by x-rays, a photon flux arriving at a detector is reduced to not less than $10^6$ photons/(s*/mm$^2$).

48. The method of claim 31, further comprising:
selecting an upper limit of the second energy range between the peak of the energy-specific absorption coefficient at a K-edge of the opacifying element and the next higher in terms of energy maximum of the DER between tissue and contrast-medium enhanced tissue.

49. The method of claim 31, further comprising:
performing optical scanning of a contour of the breast.

50. The method of claim 49, wherein the performing optical scanning includes optical scanning using at least one LASER scanner, arranged on a rotating apparatus.

51. The method of claim 31, further comprising:
determining the thickest tissue layer to be penetrated by the X-rays automatically.

52. The method of claim 31, further comprising:
determining, during a CT scan, the attenuation of the X-rays specifically for the first energy range.

53. The method of claim 52, further comprising:
simultaneously performing a first CT scan using a first radiator-detector system and a second CT scan using a second radiator-detector system, the first radiator-detector system having an angular offset with respect to the second radiator-detector system, and each of the first CT scan and the second CT scan having a different second energy range.

54. The method of claim 52, further comprising:
performing a CT scan; and
measuring, using an energy range resolving detector, attenuations at least two different energy ranges.

55. The method of claim 54, wherein the energy range resolving detector is at least one direct-converting detector.

56. The method of claim 52, further comprising:
performing a material breakdown of tomographic mammography images into at least two materials using energy-range specific attenuation.

57. The method of claim 56, wherein performing the material breakdown comprises:
breaking the tomographic images down into at least two of soft tissue, calcium and contrast medium.

58. The method of claim 31, further comprising:
performing, with a radiation detector system, two CT scans, each with a differently set second energy range.

59. The method of claim 31, further comprising:
performing a CT scan using at least two radiator-detector systems arranged with an angular offset.

60. The method of claim 31, wherein the prefiltering includes prefiltering with an element used as the opacifying element in the contrast medium.

61. The method of claim 31, further comprising:
generating a time series including a plurality of chronologically successive tomographic mammography CT images with same image parameters.

62. The method of claim 61, further comprising:
determining at least one first time constant in the time series which describes a time response of an inflow of the contrast medium.

63. The method of claim 62, further comprising:
determining a dwell time of the contrast medium in the tissue as one of the at least one first time constant.

64. The method of claim 62, wherein the determining at least one first time constant includes determining the at least one time constant volume specifically over the volume of the breast.

65. The method of claim 64, further comprising:
outputting values of the at least one first time constant in a tomographic representation.

66. The method of claim 65, further comprising:
displaying a tomographic mammography CT representation superimposed with the tomographic representation of the at least one first time constant.

67. The method of claim 66, wherein the displaying comprises:
displaying the CT values of the tomographic mammography CT representation in black and white; and
displaying the at least one first time constant in color.

68. The method of claim 62, further comprising:
determining at least one second time constant in the time series which describes the time response of the outflow of contrast medium.

69. The method of claim 61, further comprising:
determining at least one second time constant in the time series which describes the time response of an outflow of the contrast medium.

70. The method of claim 69, wherein the determining at least one second time constant includes determining the dwell time of the contrast medium in the tissue as the at least one second time constant.

71. The method of claim 69, wherein the determining at least one second time constant includes determining the at least one second time constant volume-specifically over the volume of the breast.

72. A computer configured to execute program code segments, comprising:
a memory for storing the program code segments, the program code segments, during operation of the computer, executing the method of claim 31.

* * * * *